(12) United States Patent
Coburn et al.

(10) Patent No.: US 9,226,499 B2
(45) Date of Patent: Jan. 5, 2016

(54) PROTECTED ANTIMICROBIAL COMPOUNDS FOR HIGH TEMPERATURE APPLICATIONS

(75) Inventors: Charles E. Coburn, Vernon Hills, IL (US); Michael V. Enzien, Lisle, IL (US); Heather R. Mcginley, Highland Park, IL (US); David W. Moore, Hebron, IL (US)

(73) Assignee: Dow Global Technologies LLC, Midland, MI (US)

( * ) Notice: Subject to any disclaimer, the term of this patent is extended or adjusted under 35 U.S.C. 154(b) by 198 days.

(21) Appl. No.: 13/993,574

(22) PCT Filed: Nov. 29, 2011

(86) PCT No.: PCT/US2011/062307
§ 371 (c)(1),
(2), (4) Date: Jun. 12, 2013

(87) PCT Pub. No.: WO2012/082350
PCT Pub. Date: Jun. 21, 2012

(65) Prior Publication Data
US 2013/0267604 A1    Oct. 10, 2013

Related U.S. Application Data

(60) Provisional application No. 61/424,192, filed on Dec. 17, 2010.

(51) Int. Cl.
| | |
|---|---|
| *A01N 35/10* | (2006.01) |
| *A01N 35/02* | (2006.01) |
| *C02F 1/50* | (2006.01) |
| *D21H 21/36* | (2006.01) |
| *C02F 103/02* | (2006.01) |
| *C02F 103/10* | (2006.01) |
| *C02F 103/28* | (2006.01) |
| *C02F 103/36* | (2006.01) |

(52) U.S. Cl.
CPC .............. *A01N 35/10* (2013.01); *A01N 35/02* (2013.01); *C02F 1/50* (2013.01); *D21H 21/36* (2013.01); *C02F 2103/023* (2013.01); *C02F 2103/10* (2013.01); *C02F 2103/28* (2013.01); *C02F 2103/365* (2013.01); *C02F 2303/04* (2013.01); *C02F 2303/20* (2013.01); *C09K 2208/00* (2013.01)

(58) Field of Classification Search
None
See application file for complete search history.

(56) References Cited

U.S. PATENT DOCUMENTS

| | | | |
|---|---|---|---|
| 4,107,312 A | 8/1978 | Wegner et al. | |
| 7,319,131 B2 * | 1/2008 | Swedo et al. ................. | 528/129 |

OTHER PUBLICATIONS

Power, "Aldehydes as biocides", Progress in Medicinal Chem., vol. 34, pp. 149-201 (1997).
Camehn, "New NO donors with antithrombotic and vasodilating activityes. Part 29: N-(1-Cyanocyclohexyl)-C-phenylnitrones and Glyoxaldinitrones", Archiv Der Pharmazie, vol. 333, No. 5, pp. 130-134 (2000).
Hara, "Cycloaddition reactions of a 3-(1, 3-butadienyl)cephalosporin and", J. Antibiotics, vol. 49, No. 11, pp. 1182-1185 (1996).

* cited by examiner

*Primary Examiner* — Svetlana M Ivanova
(74) *Attorney, Agent, or Firm* — Tifani M. Edwards

(57) ABSTRACT

Provided are protected antimicrobial compounds which are useful for controlling microorganisms in aqueous or water-containing systems, such as oil or gas field fluids, at elevated temperature. The antimicrobial compounds are of the formula I:

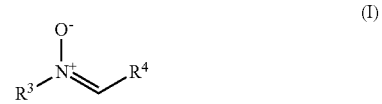

wherein $R_3$ and $R_4$ are as defined herein.

5 Claims, No Drawings

PROTECTED ANTIMICROBIAL COMPOUNDS FOR HIGH TEMPERATURE APPLICATIONS

CROSS-REFERENCE TO RELATED APPLICATION

This application claims priority from provisional application Ser. No. 61/424,192, filed Dec. 17, 2010, which is incorporated herein by reference in its entirety.

FIELD OF THE INVENTION

The invention relates to protected antimicrobial compounds and methods of their use for the control of microorganisms in aqueous or water-containing systems.

BACKGROUND OF THE INVENTION

Protecting aqueous systems from microbial contamination is critical to the success of many industrial processes, including oil or natural gas production operations. In oil and gas operations, microorganism contamination from both aerobic and anaerobic bacteria can cause serious problems such as reservoir souring (mainly caused by anaerobic sulfate-reducing bacteria (SRB)), microbiologically influenced corrosion (MIC) on metal surfaces of equipment and pipelines, and degradation of polymer additives.

Various aldehyde compounds, including formaldehyde, glutaraldehyde, and glyoxal, are known antimicrobials that are used to control the growth of microorganisms in aqueous systems and fluids, including those found in oil and gas operations. The materials, however, are susceptible to a number of drawbacks. For instance, they can degrade over time at the elevated temperatures often encountered in the oil and gas production environment. The materials can also be inactivated by other common oilfield chemicals such as bisulfite salts and amines. These conditions can leave oilfield infrastructure (wells, pipelines, etc.) and formations susceptible to microbial fouling.

It would be an advance in the art if new antimicrobial systems, which provided improved thermal and chemical stability, were developed.

BRIEF SUMMARY OF THE INVENTION

The invention provides methods for controlling microorganisms in aqueous or water-containing systems having a temperature of at least 40° C. The method comprises contacting the aqueous or water-containing system with a protected antimicrobial compound as described herein.

The invention also provides protected antimicrobial compounds that are useful for controlling microorganisms in aqueous or water-containing systems having a temperature of at least 40° C.

DETAILED DESCRIPTION OF THE INVENTION

As noted above, the invention provides compounds and methods of using them for the control of microorganisms in aqueous or water-containing systems, including those found in oil and gas operations. The invention uses protected antimicrobial compounds that release formaldehyde, glyoxal, or glutaraldehyde when heat-activated. Unlike the free aldehydes, however, the protected compounds are more stable at elevated temperatures thus permitting extended control of microbial fouling. In addition, the protected compounds may exhibit improved stability in the presence of other chemical species that would otherwise degrade the free aldehydes, such as bisulfites, and amines.

The protected antimicrobial compound for use in the methods of the invention may be represented by the formula I:

(I)

wherein $R^3$ is $C_1$-$C_6$ alkyl; and $R^4$ is H or is a group of formula:

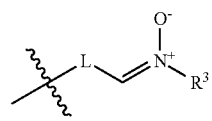

wherein L is a bond or is n-propylene.

Protected antimicrobial compounds of formula I are suitable for releasing formaldehyde, glyoxal, or glutaraldehyde, according to the methods of the invention.

Preferred compounds of formula I include compounds of formula I-1, which are compounds of formula I wherein $R^4$ is H.

Preferred compounds of formula I include compounds of formula I-2, which are compounds of formula I wherein $R^4$ is:

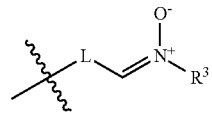

wherein L is a bond or is n-propylene.

Preferred compounds of formula I-2 include compounds of formula I-3, which are compounds of formula I-2 wherein L is a bond.

Preferred compounds of formula I-2 also include compounds of formula I-4, which are compounds of formula I-2 wherein L is n-propylene ($-CH_2CH_2CH_2-$).

Preferred compounds of formulae I, I-1, I-2, I-3, and I-4 include compounds of formula I-5, which are compounds of formula I, I-1, I-2, I-3, or I-4 wherein $R^3$ at each occurrence is $C_1$-$C_4$ alkyl. In some embodiments, $R^3$ at each occurrence is methyl. In some embodiments, $R^3$ at each occurrence is ethyl. In some embodiments, $R^3$ at each occurrence is iso-propyl. In some embodiments, $R^3$ at each occurrence is n-propyl. In some embodiments, $R^3$ at each occurrence is tert-butyl.

Exemplary compounds of formula I include the following:

| Name | Structure |
|---|---|
| N-methylene-methanamine oxide | 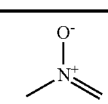 |
| N-methylene-ethanamine oxide | 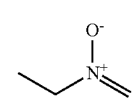 |

| Name | Structure |
|------|-----------|
| N-methylene-propylamine oxide | 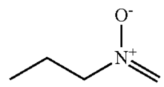 |
| N-methylene-isopropylamine oxide | 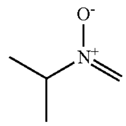 |
| N-methylene-tertbutylamine oxide | 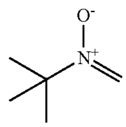 |
| N,N'-(pentane-1,5-diylidene)bis(methanamine oxide) | 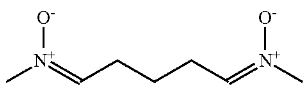 |
| N,N'-(pentane-1,5-diylidene)bis(ethanamine oxide) | 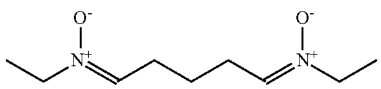 |
| N,N'-(pentane-1,5-diylidene)bis(propylamine oxide) | 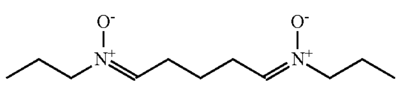 |
| N,N'-(pentane-1,5-diylidene)bis(propane-2-amine oxide) | 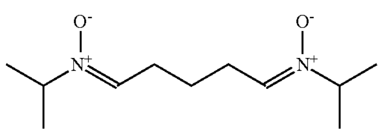 |
| N,N'-(pentane-1,5-diylidene)bis(2-methylpropan-2-amine oxide | 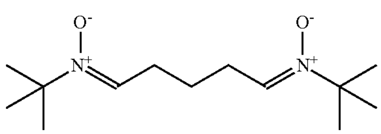 [SMILES: CC(C)(C)/[N+]([O-])=C/CCC/C=[N+](\[O-])C(C)(C)C] |
| N,N'-(ethane-1,2-diylidene)bis(methanamine oxide) | 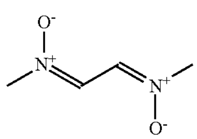 |
| N,N'-(ethane-1,2-diylidene)bis(ethanamine oxide) | 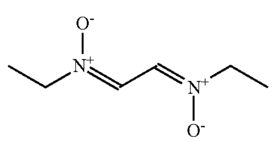 |
| N,N'-(ethane-1,2-diylidene)bis(propan-2-amine oxide) | 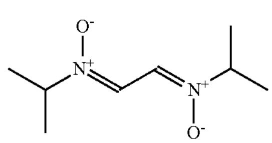 |
| N,N'-(ethane-1,2-diylidene)bis(2-methylpropan-2-amine oxide) | |

In some embodiments, the protected antimicrobial compound of formula I is N,N'-(pentane-1,5-diylidene)bis(propan-2-amine oxide).

Compounds of formula I may be prepared, for example, as depicted in Scheme I. Typically, the antimicrobial aldehyde of interest (formaldehyde, glyoxal or glutaraldehyde) is mixed with hydroxylamine compound B in a suitable solvent, such as water. The mixture may be stirred and continued for sufficient time to allow the reaction to occur and the desired compound of formula I to form. The product may be used as is, or optionally further purified using techniques well known to those skilled in the art, such as crystallization, chromatography, distillation, etc.

SCHEME I

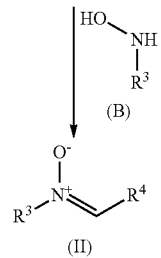

Examples of hydroxylamine compounds B that may suitably used in the invention include, but are not limited to, N-methylhydroxylamine, N-ethylhydroxylamine, N-propylhydroxylamine, N-isopropylhydroxylamine, and N-tertbutylhydroxylamine.

Some of the protected antimicrobial compounds of formula I are novel. Thus, in a further embodiment, the invention provides novel compounds of formula I. In some embodiments, the compound is N-methylenemethanamine oxide. In some embodiments, the compound is N,N'-(pentane-1,5-diylidene)bis(methanamine oxide). In some embodiments, the compound is N,N'-(pentane-1,5-diylidene)bis(ethanamine oxide). In some embodiments, the compound is N,N'-(pentane-1,5-diylidene)bis(propylamine oxide). In some embodiments, the compound is N,N'-(pentane-1,5-diylidene)bis(propan-2-amine oxide). In some embodiments, the compound is N,N'-(pentane-1,5-diylidene)bis(2-methylpropan-2-amine oxide). In some embodiments, the compound is N,N'-(ethane-1,2-diylidene)bis(ethanamine oxide). In some embodiments, the compound is N,N'-(ethane-1,2-diylidene)bis(propan-2-amine oxide). In some embodiments, the compound is N,N'-(ethane-1,2-diylidene)bis(2-methylpropan-2-amine oxide).

The protected antimicrobial compounds described herein release antimicrobial aldehydes (formaldehyde, glyoxal, or glutaraldehyde) when heat-activated. Unlike the free aldehydes, however, the protected compounds are more stable at elevated temperatures thus permitting extended control of microbial fouling. In addition, the protected compounds may exhibit improved stability in the presence of other chemical species that would otherwise degrade the free aldehydes, such as bisulfites, and amines.

Because of their stability and heat activation characteristics, the protected antimicrobial compounds of the invention are useful for controlling microorganisms for extended periods of time in aqueous or water-containing systems that are at elevated temperatures, including those that may be present or used in oil or natural gas applications, paper machine white water, industrial recirculating water, starch solutions, latex emulsions, hot rolling machining fluids, or industrial dishwashing or laundry fluids. In some embodiments, the aqueous or water-containing system may be present or used in oil or natural gas applications. Examples of such systems include, but are not limited to, fracturing fluids, drilling fluids, water flood systems, and oil field water.

In some embodiments, the aqueous or water-containing system may be at a temperature of may be activated at 40° C. or greater, alternatively 55° C. or greater, alternatively 60° C. or greater, alternatively 70° C. or greater, or alternatively 80° C. or greater.

In addition to their heat stability, the compounds may further be effective when a deactivating agent, such as a source of bisulfite ion or amines is present in the system.

A person of ordinary skill in the art can readily determine, without undue experimentation, the concentration of the protected antimicrobial compound that should be used in any particular application. By way of illustration, a suitable concentration, based on the equivalent of antimicrobial aldehyde that is potentially released (assuming 100% release) by the protected compound is typically at least about 1 ppm, alternatively at least about 5 ppm, alternatively at least about 50 ppm, or alternatively at least about 100 ppm by weight. In some embodiments, the concentration is 2500 ppm or less, alternatively 1500 ppm or less, or alternatively 1000 ppm or less. In some embodiments, the aldehyde equivalent concentration is about 100 ppm.

The protected antimicrobial compounds may be used in the system with other additives such as, but not limited to, surfactants, ionic/nonionic polymers and scale and corrosion inhibitors, oxygen scavengers, nitrate or nitrite salts, and/or additional antimicrobial compounds.

For the purposes of this specification, the meaning of "microorganism" includes, but is not limited to, bacteria, fungi, algae, and viruses. The words "control" and "controlling" should be broadly construed to include within their meaning, and without being limited thereto, inhibiting the growth or propagation of microorganisms, killing microorganisms, disinfection, and/or preservation against microorganism re-growth. In some embodiments, the microorganisms are bacteria. In some embodiments, the microorganisms are aerobic bacteria. In some embodiments, the microorganisms are anaerobic bacteria. In some embodiments, the microorganisms are sulfate reducing bacteria (SRB).

"Alkyl," as used in this specification encompasses straight and branched chain aliphatic groups having the indicated number of carbon atoms. Exemplary alkyl groups include, without limitation, methyl, ethyl, propyl, isopropyl, butyl, isobutyl, sec-butyl, tert-butyl, pentyl, and hexyl.

The following examples are illustrative of the invention but are not intended to limit its scope. Unless otherwise indicated, the ratios, percentages, parts, and the like used herein are by weight.

EXAMPLES

Example 1

Preparation of N,N'-(pentane-1,5-diylidene)bis(propan-2-amine oxide) ("IPHA adduct")

Into a 250 ml round-bottomed flask (RBF) equipped with a nitrogen inlet, a magnetic stirrer, and an addition funnel is added a 19.6 wt % aqueous solution of isopropylhydroxylamine (IPHA, 56.1 g, 11.0 g actives, 0.147 mols). This is cooled (3° C.) by a dry ice bath to afford a white slurry. A solution of 50% aqueous glutaraldehyde (13.3 g, 6.66 g actives, 0.066 mols, 0.45 equivalence) is added by an addition funnel. Shortly after the glutaraldehyde addition is completed, a sample is taken and analyzed by GC to confirm that the glutaraldehyde has been consumed.

The crude aqueous IPHA-Glut adduct solution may be purified, if desired, for example by extracting with EtOAc (1:1 ratio) to reduce the concentration of residual IPHA. Then EtOAc (1:1 ratio) is added and heated to reflux before being decanted away from the aqueous phase. The EtOAc phase is cooled and concentrated in vacuo to afford a hygroscopic yellow sticky solid (14.2 g, 99.5% yield). This is dissolved into hot ether (150 ml) and vacuum filtered to afford an orange solution (75 ml) that is diluted with a little pentane and seeded with the yellow sticky solid. Since this results in product oiling out, the ether/pentane solution is cooled to −78° C. (dry-ice bath) to solidify. This results in two distinct solids (light yellow and orange) solidifying that are vacuum filtered under nitrogen which affords only the light yellow solid at room temperature.

The light yellow solid is isolated and dried under high vacuum (0.3 torr) for several hours to remove the solvents and excess IPHA. The resulting amorphous light yellow solid (4.0 g, 28% yield, 98.6% purity) is stored under nitrogen and has a melting point of 78.5° C. (wets), 81.0-85.0° C. melts. The mother liquors are combined and concentrated to afford an orange oil (10.3 g, 72% yield, 92.4% purity). Spectral analysis confirms the presence of the desired compound. GC/MS (CI mode) analysis shows [MH]$^+$ m/z 158. $^1$H NMR (CD$_3$OD, ppm): 1.357-1.390 (m), 1.797 (m), 2.484 (m), 4.184 (m), 7.258 (t). 13C NMR (CD$_3$OD, ppm): 30.808, 32.266, 37.251, 77.179, 152.282.

Example 2

Analysis of Glutaraldehyde Release

Samples of the IPHA-adduct are analyzed for glutaraldehyde content. Samples are prepared in sterile deionized water at the molar equivalent of 2000 ppm glutaraldehyde. A standard of 500 ppm glutaraldehyde is also prepared. An initial measurement is taken just after sample preparation. Samples are then heat-aged at 55° C. for 2 h or 24 h and analyzed again. Glutaraldehyde concentration is measured directly via GC and after pre-column derivatization by HPLC. No glutaraldehyde is detected by GC. HPLC shows low levels of glutaraldehyde. These results are consistent with the reaction products being stable to elevated temperature but with slight degradation in the presence of the acidic conditions required for derivatization and HPLC analysis.

Example 3

Assay for Biocidal Efficacy

Purified adduct from Example 1, adduct reaction mixtures ("crude adduct"), and the protective component alone (IPHA)

are tested for biocidal activity against a pool of aerobic organisms at room temperature and against sulfate reducing bacteria (SRB) at 40° C. Tests are performed as follows:

a. Aerobic Bacteria. A mixed pool of 6 bacterial species at approximately $5\times10^6$ CFU/mL in phosphate buffered saline is introduced into a 96-well plate (1 mL/well). Each well receives an independent chemical treatment (i.e. adduct, protective component, glutaraldehyde, etc. at varied concentrations). The remaining cell density in each well is then measured at given timepoints by dilution to extinction in a medium containing resazurin dye as an indicator.

It is found that none of the adducts or protective groups is biocidal at concentrations equivalent to up to 300 ppm glutaraldehyde by weight.

b. Thermophilic Bacteria. A 48-72 hour old culture of *T. thermophilus* is pelleted by centrifuging at 2000 g and the pellet resuspended in 10 times the culture volume of buffer (PBS or carbonate-buffered synthetic freshwater). The suspension is distributed into 10 mL aliquots in glass screw-cap tubes. Each tube is then treated with glutaraldehyde or an adduct and incubated at 70° C. At indicated timepoints, cell density in each tube is measured via dilution to extinction by serially diluting a sample and plating dilutions on solid media.

Results:

(1) Samples treated with the equivalent of 100 ppm glutaraldehyde exhibit greater than 5-log lower CFU/mL than untreated samples after 24 h exposure to the adducts or glutaraldehyde. Subsequent re-challenging of the biocides by adding more bacteria also exhibits greater than 5-log reduction in CFU/mL after 24 h exposure. After 5 days, glutaraldehyde fails to control bacterial levels. In contrast, the IPHA-adduct maintains greater than 5-log reduction in CFU/mL over the course of 18 days and 2 to 3-log reduction over 5 weeks.

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:

1. A method for controlling microorganisms in an aqueous system having a temperature of at least 40° C., the method comprising contacting the aqueous system with a protected antimicrobial compound of a formula I:

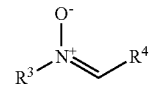

(I)

wherein $R^3$ is $C_1$-$C_6$ alkyl; and
$R^4$ is H or is a group of formula:

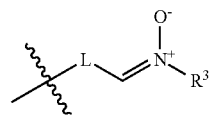

wherein L is a bond or is n-propylene;
further wherein the aqueous system is oil or as field fluid, paper machine white water, industrial recirculating water, starch solution, latex emulsion, hot rolling machining fluid, or industrial dishwashing or laundry fluid; and
still further wherein the oil or gas field fluid is fracturing fluid, drilling fluid, water flood system, or oil field water.

2. The method according to claim 1 wherein $R^4$ is:

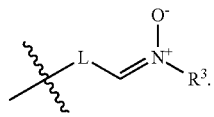

3. The method according to claim 2 wherein L is n-propylene (—$CH_2CH_2CH_2$—).

4. The method according to claim 1 wherein $R^3$ at each occurrence is $C_1$-$C_4$ alkyl.

5. The method according to claim 1 wherein the compound of formula I is: N-methylenemethanamine oxide; N-methyleneethanamine oxide; N-methylenepropylamine oxide; N-methyleneisopropylamine oxide; N-methylenetertbutylamine oxide; N,N'-(pentane-1,5-diylidene)bis(methanamine oxide); N,N'-(pentane-1,5-diylidene)bis(ethanamine oxide); N,N'-(pentane-1,5-diylidene)bis(propylamine oxide); N,N'-(pentane-1,5-diylidene)bis(propan-2-amine oxide); (pentane-1,5-diylidene)bis(2-methylpropan-2-amine oxide); N,N'-(ethane-1,2-diylidene)bis(methanamine oxide); N,N'-(ethane-1,2-diylidene)bis(ethanamine oxide); N,N'-(ethane-1,2-diylidene)bis(propan-2-amine oxide); N,N'-(ethane-1,2-diylidene)bis(2-methylpropan-2-amine oxide); or mixtures of two or more thereof.

* * * * *